US010138030B2

(12) United States Patent
Orszullok

(10) Patent No.: US 10,138,030 B2
(45) Date of Patent: Nov. 27, 2018

(54) TAMPERPROOF CLOSURE FOR USE ON A CONTAINER, CONTAINER THEREWITH, AND PORT FOR ARRANGEMENT ON THE CONTAINER

(71) Applicant: B. BRAUN AVITUM AG, Melsungen (DE)

(72) Inventor: Willy Orszullok, Neuenrade (DE)

(73) Assignee: B. BRAUN AVITUM AG, Melsungen (DE)

( * ) Notice: Subject to any disclaimer, the term of this patent is extended or adjusted under 35 U.S.C. 154(b) by 231 days.

(21) Appl. No.: 14/427,216

(22) PCT Filed: Sep. 19, 2013

(86) PCT No.: PCT/EP2013/069531
§ 371 (c)(1),
(2) Date: Mar. 10, 2015

(87) PCT Pub. No.: WO2014/048843
PCT Pub. Date: Apr. 3, 2014

(65) Prior Publication Data

US 2015/0246757 A1 Sep. 3, 2015

(30) Foreign Application Priority Data

Sep. 27, 2012 (DE) ........................ 10 2012 109 194

(51) Int. Cl.
*A61B 50/00* (2016.01)
*B65D 43/02* (2006.01)
(Continued)

(52) U.S. Cl.
CPC ........ *B65D 43/0277* (2013.01); *A61J 1/1412* (2013.01); *B65D 41/0485* (2013.01);
(Continued)

(58) Field of Classification Search
CPC .............. B65D 43/0277; B65D 43/267; B65D 41/0485; B65D 47/36; B65D 2543/00888;
(Continued)

(56) References Cited

U.S. PATENT DOCUMENTS 605,482 A * 6/1898 Jaggard .............. B65D 41/0485 215/302
621,161 A * 3/1899 Shaw ................... B65D 1/0238 215/47
(Continued)

FOREIGN PATENT DOCUMENTS

CN 2827922 10/2006
CN 201027022 2/2008
(Continued)

OTHER PUBLICATIONS

Office Action with Search Report for Chinese Application CN 2013800503273 dated Nov. 27, 2015, with translation.
(Continued)

*Primary Examiner* — Jacob K Ackun
*Assistant Examiner* — Jenine Pagan
(74) *Attorney, Agent, or Firm* — RatnerPrestia

(57) ABSTRACT

Tamperproof closures for use on a container are disclosed. The closure includes a base which can be arranged on a container port and can be connected thereto in a fluid-tight manner as well as a closure part connected to the base via a predetermined breaking point. Each of the base and the closure part includes at least one force-enhancing means by which a movement of the base and the closure part relative to each other can be force-assisted in terms of destruction of the predetermined breaking point. The movement of the base and the closure part relative to each other can be a rotary movement of the closure part with respect to the base in the opening direction of the closure part and each force-enhanc-
(Continued)

ing means can be a handle in the form of a lever projecting radially from both the base and the closure part with respect to the axis of rotation of the rotary movement.

19 Claims, 3 Drawing Sheets

(51) Int. Cl.

| | |
|---|---|
| ***B65D 41/04*** | (2006.01) |
| ***B65D 47/36*** | (2006.01) |
| ***A61J 1/14*** | (2006.01) |
| ***B65D 43/26*** | (2006.01) |

(52) U.S. Cl.
CPC ........... *B65D 43/267* (2013.01); *B65D 47/36* (2013.01); *B65D 2543/00888* (2013.01)

(58) Field of Classification Search
CPC . B65D 5/70; B65D 5/54; B65D 51/20; B65D 39/16; B65D 5/24; B65D 51/243; B65D 2251/02; A61J 1/1412
USPC ............ 220/212, 212.5, 285, 284, 253, 256, 220/DIG. 34; 215/304, 305, 253, 256, 215/901, 295, 313; 206/807, 1.5; 222/541.6, 541.9; 81/3.15, 3.09, 3.57, 81/3.55, 3.56, 3.49, 3.27
See application file for complete search history.

(56) References Cited

U.S. PATENT DOCUMENTS

| | | | | | |
|---|---|---|---|---|---|
| 3,278,063 | A * | 10/1966 | Kranzhoff | B65D 51/002 | 215/247 |
| 3,591,031 | A * | 7/1971 | Komendowski | B65D 1/0238 | 215/250 |
| 4,463,862 | A * | 8/1984 | Hansen | A61J 1/1412 | 215/232 |
| 5,088,613 | A * | 2/1992 | Dutt | B65D 47/242 | 215/250 |
| 5,114,030 | A | 5/1992 | Conard | | |
| 5,507,419 | A * | 4/1996 | Martin | B65D 21/0235 | 222/480 |
| 5,992,657 | A * | 11/1999 | Friedman | B65D 41/3409 | 215/209 |
| 6,485,479 | B1 | 11/2002 | Knierbein | | |
| 6,571,971 | B1 | 6/2003 | Weiler | | |
| 7,374,357 | B2 * | 5/2008 | Takahashi | A61C 5/066 | 215/296 |
| 8,522,994 | B2 * | 9/2013 | Weiler | B65D 1/095 | 215/256 |
| 8,585,674 | B2 | 11/2013 | Brandenburger et al. | | |
| 8,714,381 | B2 * | 5/2014 | Bernhard | B01L 3/523 | 215/228 |
| 9,133,972 | B2 * | 9/2015 | Sridhar | B65D 1/095 | |
| 2009/0054865 | A1 | 2/2009 | Brandenburger et al. | | |

FOREIGN PATENT DOCUMENTS

| | | |
|---|---|---|
| CN | 101600627 | 12/2009 |
| DE | 197 28 775 | 1/1999 |
| DE | 197 17 765 | 2/1999 |
| DE | 102 05 344 | 9/2002 |
| DE | 10 2004 051 300 | 11/2005 |
| DE | 10 2008 060 864 | 6/2010 |
| EP | 2 277 784 | 1/2011 |
| JP | 2007 099303 | 4/2007 |
| JP | 2010222022 | 10/2010 |

OTHER PUBLICATIONS

International Search Report for PCT/EP2013/069531 dated Jan. 2, 2014.
German Search Report for DE 10 2012 109 194.3 dated Jul. 16, 2013.

* cited by examiner

TAMPERPROOF CLOSURE FOR USE ON A CONTAINER, CONTAINER THEREWITH, AND PORT FOR ARRANGEMENT ON THE CONTAINER

CROSS REFERENCE TO RELATED APPLICATIONS

This application is the U.S. national phase application of PCT International Application No. PCT/EP2013/069531 filed Sep. 19, 2013, which claims priority to German Patent Application No. DE 10 2012 109 194.3 filed Sep. 27, 2012, the contents of each application being incorporated by reference herein.

FIELD OF THE INVENTION

The present invention relates to a tamperproof closure for use on a container, especially a (fluid) container for medical fluids having at least one port on which such tamperproof closure is arranged, as well as to a port for arrangement/configuration on such container.

BACKGROUND

For safely sealing containers, especially but not exclusively containers for medical purposes or food packages, it is frequently indispensable to equip the container with a tamperproof closure so that unauthorized opening of the container closure and thus possible uselessness of the content for the intended purpose can be indicated.

For this purpose, different designs of tamperproof or guarantee closures have already become known.

It is known, for example, to hold a respective container with one hand as a counter-bearing, while the other hand opens or removes the tamperproof closure by turning, tearing, breaking off or any other separating operation while destroying a safety element in the form of a predetermined breaking line or predetermined rupturing line. Hence for opening or removing ("breaking") the tamperproof closure two hands are necessary, especially when smaller lightweight or flexible containers are concerned which are not adapted to provide sufficient counter-bearing by their low deadweight during the opening operation of the tamperproof closure.

When containers for medical purposes are opened, in practice it frequently happens, however, that the user performs an important activity by one hand and simultaneously has to open the tamperproof closure (for example for an infusion solution) by the other hand. In such case the user is either forced to shortly interrupt the activity already performed by the one hand so as to get both hands free for opening the tamperproof closure, or he/she has to ask another person in the vicinity to either at least hold the container or to right away open the container himself/herself.

This is complicated and includes risks, as the presence of a further person cannot be ensured under all circumstances, for example, and the person who has to act alone might have to take risky steps so as to be able to open the container.

In view of these problems, it is an object of the present invention to configure a tamperproof closure for use on a container so that said tamperproof closure can also be operated, namely, opened, by one person and especially by one hand only.

SUMMARY OF THE INVENTION

For achieving this object the present invention suggests a tamperproof closure for use on a (fluid) container comprising a base adapted to be arranged (arranged) on a container port and connectable (connected) thereto in a fluid-tight manner as well as a closure part connected to the base (by adhesive bonding) via a predetermined breaking point. In accordance with the invention, each of the base and the closure part has at least one force-enhancing means (operating lever) by which a movement of the base and the closure part relative to each other can be force-assisted in terms of destruction of the predetermined breaking point and thus can be performed single-handed.

The force-enhancing means enable the base and the closure part to be moved relative to each other (by one hand) without having to hold the container on which the base is arranged indirectly via the container port. The force transmission when the base and the closure part are moved relative to each other so as to remove the closing state by destroying the predetermined breaking point is effectuated directly via the force-enhancing means (finger levers) on the base and the closure part so that the movement of the base and the closure part relative to each other can be triggered and carried out single-handed.

The relative movement of the base and the closure part preferably is a rotary motion of the closure part vis-à-vis the base in the opening direction of the closure part. In particular, but not exclusively, the base and the closure part can be in screwing engagement so that, in the case of twisting the closure part against the base, the screwed connection requires an axial connection of the closure part vis-à-vis the base in addition to the rotary movement so that the predetermined breaking point is broken.

Each force-enhancing means preferably is in the form of a handle (lever or button) substantially radially projecting from both the base and the closure part with respect to the axis of rotation of the rotary movement. This ensures unhindered access, i.e. easy grasping, of the force-enhancing means with the fingers (thumb and index) of a human hand, even if the haptics of a user is restricted for example by wearing gloves.

The handles preferably enclose an angle there between in the circumferential direction of the tamperproof closure which corresponds at least to the amount of rotation of the closure part vis-à-vis the base for destroying the predetermined breaking point. This means that by actuating the handles a (relative) rotary movement between the closure part and the base is brought about (namely, by moving the levers/buttons toward each other) which extends at least on the peripheral side over such angular amount that the predetermined breaking point is destroyed.

The angle may be within a range of about 20° to 50°, preferably within a range of about 30° to 40°. With a relative rotation between the base and the closure part angles of less than 20° usually do not ensure a sufficient amount of rotation which may result in the destruction of the predetermined breaking point. Angles of more than 50° frequently are no longer feasible for reasons of deteriorated handling.

The force application point on the base-side handle and the force application point on the closure part-side handle of preference are on a joint circumference around the axis of rotation of the rotary movement. By "force application point" in this context the point or area on the respective handle can be understood where the user contacts this handle so as to cause or initiate the relative movement (e.g. rotary movement) between the base and the closure part. When these two force application points are located substantially on a joint circumference around the axis of rotation of the rotary movement, i.e. substantially equally distanced from this axis of rotation viewed in the radial direction, a symmetric force transmission into the closure takes place, as the lever actions of the handles are substantially equal. The handling during the opening operation is improved in this way.

In other words, in contrast to the state of the art each force-enhancing means, according to aspects of the invention, is a handle substantially radially projecting from both the base and the closure part relative to the axis of rotation of the rotary movement preferably in the form of a lever or a button enclosing there between, viewed in the circumferential direction of the closure, an angle which corresponds at least to the amount of rotation of the closure part vis-à-vis the base for the destruction of the predetermined breaking point.

In this way both levers/buttons can be grasped by the thumb and the index of one single hand and can be pressed against each other in the circumferential direction of the base/the closure part. What is crucial in this context is that the angular distance of the two levers/buttons is at least just sufficient for breaking the predetermined breaking point and is still located within the operating range of one single hand (standard hand). It is approximately within a range of from 20° to 50°, preferably of from about 30° to 40°.

In accordance with a further advantageous aspect of the present invention, which can possibly be claimed as an independent idea, the base-side handle is formed in a top view in the form of a sector so that it projects from the closure part-side handle on both sides in the circumferential direction while enclosing an angle in the afore-mentioned range. In other words, each handle consists of two diametrically opposed, radially outwardly extending levers/buttons so that the closure can be opened from two (circumferential) sides, i.e. by the left or the right hand. In this way the tamperproof closure can be operated in both directions of rotation especially when the opening operation requires relative twisting between the base and the closure part. If the connection between the closure part and the base is not a screwed connection but for example a mere plug-in connection secured by the predetermined breaking point, the predetermined breaking point can be destroyed by rotation in both directions, which is assisted by the afore-mentioned advantageous design option of the tamperproof closure. By this advantageous configuration also the handling of the closure both by the right and the left hand is possibly facilitated.

As already indicated, on each of the base and the closure part, two handles/levers/buttons can be arranged which then are diametrically opposed to each other. This can facilitate the handling of a container provided with the tamperproof closure according to aspects of the invention.

Furthermore the subject matter of the present invention is a container, especially a container for medical fluids, wherein the container includes at least one port, a tamperproof closure according to the present invention being arranged at/in the port.

The subject matter of the present invention further is a port for being arranged on a container, especially a container for medical fluids, the port being provided with a tamperproof closure according to the present invention.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
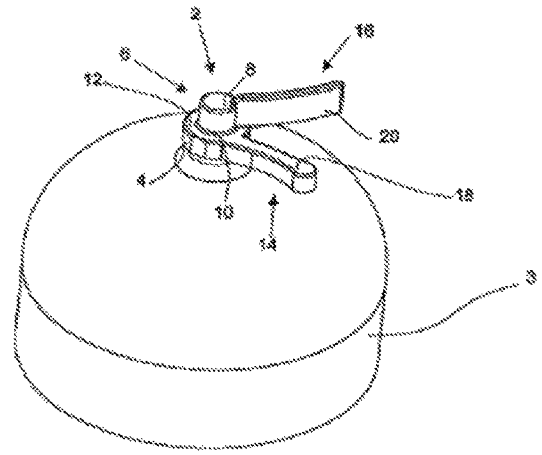
FIG. 1 shows a perspective view of a tamperproof closure according to aspects of the invention.

A tamperproof closure 2 according to the present invention (hereinafter referred to "closure") can be/is arranged at an inlet and/or outlet (port) of a container 3 for receiving e.g. fluids which is not shown in detail in the drawing. The closure 2 substantially comprises a base 4 having an outer circumference 40 adapted to be arranged/arranged on the container port and connectable/connected thereto in a fluid-tight manner, wherein the base 4 is welded, glued, pressed or otherwise connected to the port in a lasting, rotationally fixed and fluid-tight manner. On the base 4 there is provided a closure or closure part 6 which in the illustrated embodiment can substantially take the shape of a closure cap 8 adapted to cover a hollow-cylindrical inlet and/or outlet of the port which is formed on the port and passes through a respective bore in the base 4. The outer circumference of this outlet can be provided at least in portions with a male thread having a large pitch which can be engaged in a corresponding female thread at the inner circumference of the closure cap 8. By a respective relative rotation between the closure cap 8 and the base 4 the former thus can release or close the outlet on the port.

In the tamperproof state in which the container is filled and closed by the closure 2 the closure part 6 and, respectively, the closure cap 8 is fixed vis-à-vis the base 4 at an outer circumference 42 of the closure cap 8, this fixing being performed by a predetermined breaking point 10 by which the free circumferential edge of the closure cap 8 is fastened to an upper surface 12 of the base 4. This predetermined breaking point 10 can be formed by a closed circumferential ring corresponding to the outer circumference 42 of the closure cap 8, by a plurality of lands between the surface 12 and the lower edge of the cap 8 or by similar elements destroyable by the application of force.

When the closure cap 8 is in screwing engagement with the outlet, as explained in the foregoing, the predetermined breaking point 10 is destroyed upon twisting the closure cap 8 vis-à-vis the base 4 by the rotary movement along with an axial movement of the closure cap 8 due to the thread engagement so that the closure cap 8 can release the outlet.

A destroyed predetermined breaking point 10 thus is a reliable indication of the fact that a container closed by the closure 2 has been opened already at least once.

It is understood that the representation of the closure 2 according to the figures of the drawing and here especially the technical feature of the thread engagement between the closure part 6 and the outlet is only one out of plural possible configurations. Ultimately the subject matter of the present invention constitutes a tamperproof closure in which a closure part 6 has to perform a relative movement vis-à-vis a base for destroying a predetermined breaking point. Said relative movement need not necessarily be a rotary movement coupled to an axial movement, but can also be a mere axial movement, a mere rotary movement, a tilting movement or the like.

In the shown embodiment the base 4 further includes a force-enhancing means 14. Moreover the closure part 6 includes a force-enhancing means 16. Here the base-side force-enhancing means 14 is in the form of a handle (lever or button) 18 substantially radially projecting vis-à-vis the base 4 with respect to the axis of rotation of the rotary movement of the closure part 6. The force-enhancing means 16 is equally in the form of a handle (lever or button) 20 projecting radially from the outer periphery of the closure part 6 or the closure cap 8. The two handles 18 and 20 accordingly can be basically considered to be lever arms arranged at the respective outer peripheries of the base 4 and, respectively, the closure cap 8 and projecting radially outwardly herefrom.

Figure 2:
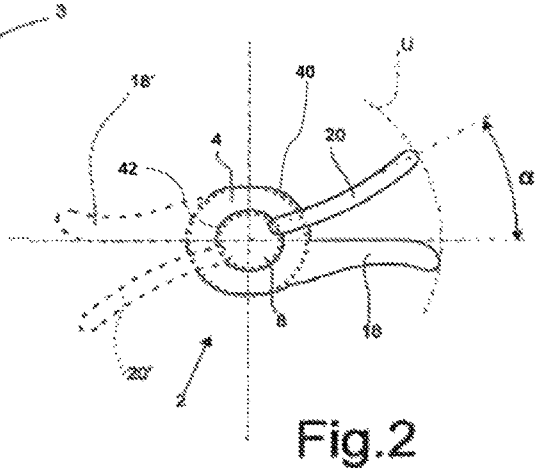
FIG. 2 is a top view of the tamperproof closure of FIG. 1.

As is especially evident from the representation of FIG. 2, the two handles 18 and 20 are not aligned or congruent with each other viewed in a top view along the axis of rotation, but viewed in the circumferential direction enclose a specific angle α between them. This angle is within a range of about 20° to 50°, preferably within a range of about 30° to 40°.

Each of the two handles 18 and 20 has such radial longitudinal extension that their free ends are substantially located on a joint circumference (orbit) U around the axis of rotation of the rotary movement. Force application points on the base-side handle and on the closure part-side handle are preferably substantially located on a further joint circumference around the axis of rotation of the rotary movement, wherein said further circumference will have a more or less smaller radius than the circumference U. By "force application point" in this context the point or else area on the respective handle 18 and 20 can be understood at which this handle is contacted by the user so as to cause or initiate the relative movement (e.g., rotary movement) between the base 4 and the closure part 6.

Figure 3:
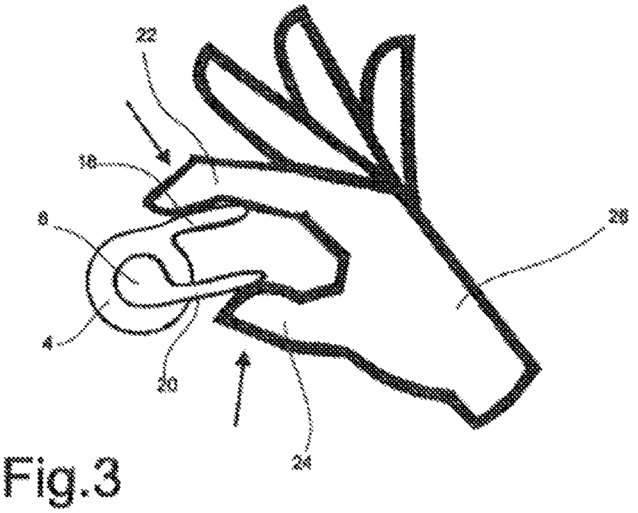
FIG. 3 schematically shows the handling of the tamperproof closure of FIG. 1 and FIG. 2.

FIG. 3 shows schematically in a top view the handling of the closure 2 according to aspects of the invention. It is evident that by grasping the two handles 18 and 20 by, e.g., the index 22 and the thumb 24 of one hand 26 and by a forceps-like or pincers-like closing movement between the thumb 24 and the index 22 in the direction of the arrows of FIG. 3 the two handles 18 and 20 are moved toward each other, wherein the handle 20 arranged on the closure part 6 or the closure cap 8 carries out a relative movement toward the base-side handle 18. Hereby the closure part 6 is twisted vis-à-vis the base 4 in terms of destruction of the predetermined breaking point 10 and the tamperproof closure 2 is broken. After destroying the predetermined breaking point 10 the closure cap 8 of the closure part 6 can be completely screwed off by the hand 26 in the known way.

If there is no screwed engagement but only a plug-in connection between the closure part 6 or the closure cap 8 and the butt-type outlet on the side of the container, the predetermined breaking point 10 can be equally destroyed by grasping and compressing the two handles 18 and 20. A guided movement between the base 4 and the closure part 6 in terms of a screwed connection is thus not mandatory.

Hence in the subject matter of the present invention the counter-bearing required for destroying the predetermined breaking point 10 is not made available indirectly via the container to which the base 4 is fixed in position but directly by the base 4 of the closure 2 itself, wherein the two handles or levers 18 and 20 enable the required relative movement between the base 4 and the closure part 6. Thus it is possible to open the closure 2 according to aspects of the invention with true single-handed operation.

Figure 4A:
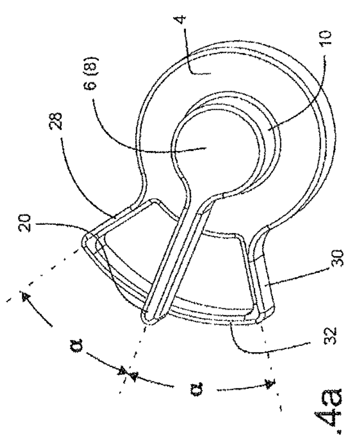
FIGS. 4A, 4B, 5A, 5B, 6A, and 6B show different views of three further configurations of the tamperproof closure according to aspects of the invention

In FIGS. 4A to 6B three further embodiments of the closure 2 according to aspects of the invention are illustrated in different views. FIG. 4A shows in a top view and FIG. 4B shows in a tilted bottom view an embodiment in which the base-side handle 18 and, respectively, the base-side force-enhancing means 14 is/are not configured in the form of a single lever but in the form of two lands 28 and 30 projecting radially outwardly from the outer periphery of the base 4 which are interconnected at their free ends via a bridge 32. Between the land 28 and the closure part-side lever or the closure part-side handle 20 again the angle α according to FIG. 2 is defined; this angle α is equally defined between the land 30 and the handle 20. Thus in the configuration of FIGS. 4A and 4B the closure part 6 and, respectively, the closure cap 8 can be twisted vis-à-vis the base 4 both clockwise and anti-clockwise in FIG. 4A, wherein the forceps-like or pincers-like grip by the thumb and the index of one hand is performed either between the land 28 and the handle 20 or between the land 30 and the handle 20.

The bridge 32 between the free ends of the lands 28 and 30 serves both for reinforcing the lands 28 and 30 and for preventing the free ends of the lands 28 and 30 from entangling in external objects, for example clothes. Moreover also the handle 20 is better protected by the bridge 32.

Figure 4B:
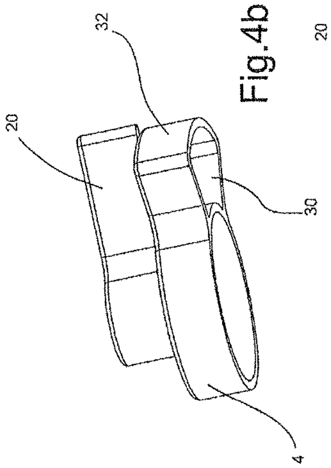
Figure 5A:
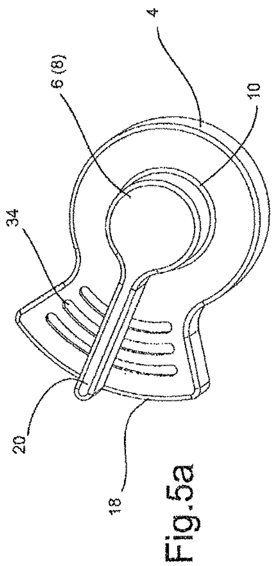

The statements made concerning the FIGS. 4A and 4B are substantially applicable also to the configurations or modifications of the FIGS. 5A to 6B. The differences from FIG. 4A and 4B reside in the configuration of the base-side handle 18 which in the embodiment of FIGS. 5A and 5B is formed to be closed/sector-shaped and, analogously to FIG. 4A, projects from the base-side handle 18 on both sides in the circumferential direction. For saving material and weight the handle 18 can be provided with one or a plurality of slit-shaped breakthroughs 34.

Figure 5B:
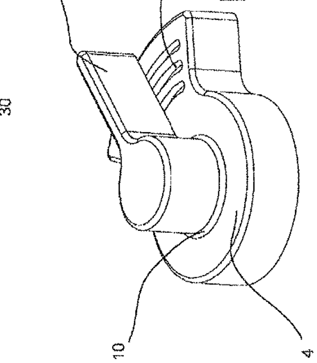
Figure 6A:
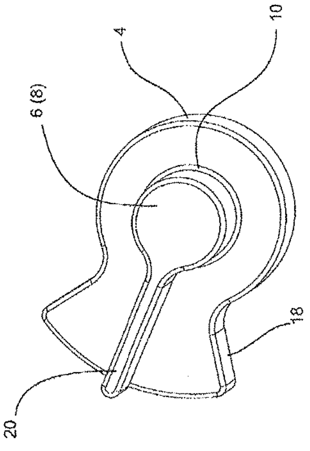
Figure 6B:
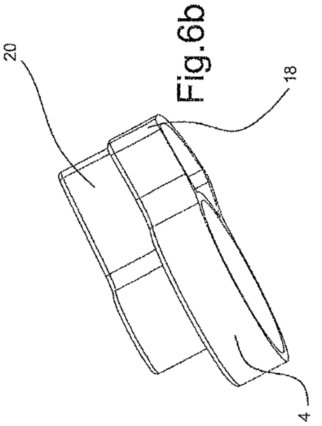

In the configuration of FIGS. 6A and 6B the breakthroughs according to FIGS. 5A and 5B are not provided so that the base-side handle 18 has a closed upper side 36.

FIG. 2 illustrates in broken lines a further configuration or modification in which both on the base 4 and on the closure part 6 two handles (18 and 18' and, respectively, 20 and 20') are arranged which equally enclose there between the angle α (or an angle deviating from this angle α, where appropriate) and which are substantially diametrically opposed to the handles 18 and 20. In this modification the closure 2 can be grasped and opened from two directions distanced from each other by approximately 180°.

Figure 7B:
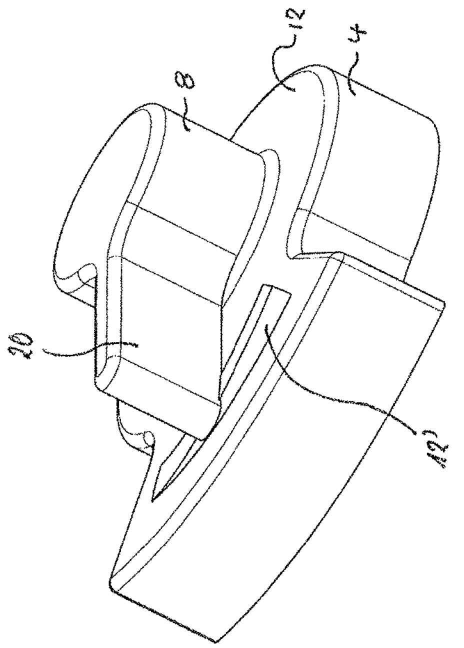
FIGS. 7*a* and 7*b* show two perspective views of a different embodiment of the tamperproof closure according to aspects of the invention illustrating a superimposed rotary and pulling movement of the closure.
Figure 7A:
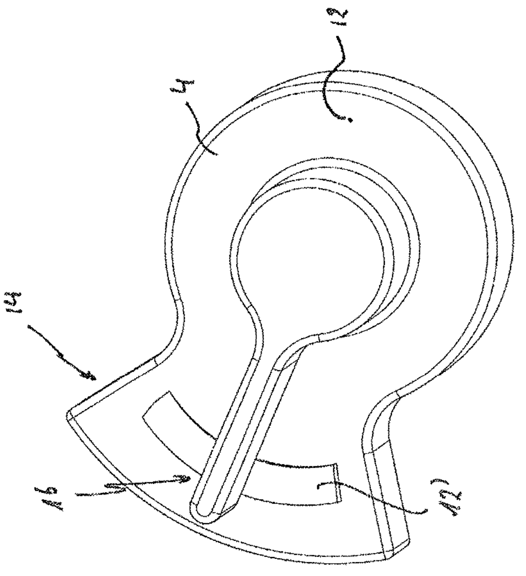

Finally, in accordance with FIGS. 7*a* and 7*b*, the surface 12 of the base 4 can be equipped with a kind of ramp 12' which is continuously raised from the surface 12 in the direction of rotation of the closure cap 8. This ramp 12' causes the lever 20 to slide over the ramp 12' during the relative movement of the cap 8 and in this way an additional force component away from the base 4 to be applied to the cap 8. Hereby the turn-off force is additionally assisted and reinforced, respectively.

Summing up, in so far there has been described a tamperproof closure for use on a container comprising a base adapted to be arranged on a container port and connectable thereto in a fluid-tight manner as well as comprising a closure part which is connected to the base via a predetermined breaking point. Each of the base and the closure part includes at least one force-enhancing means by which a movement of the base and the closure part relative to each other in terms of destruction of the predetermined breaking point can be force-assisted. The movement of the base and the closure part relative to each other can be a rotary movement of the closure part vis-à-vis the base in the opening direction of the closure part and each force-enhancing means can be a handle in the form of a lever or the like substantially radially projecting from both the base and the closure part relative to the axis of rotation of the rotary movement.

The invention claimed is:

1. A container apparatus comprising:
- a container having an opening; and
- a tamperproof closure arranged on the opening of the container, the tamperproof closure including:
  - a base having an outer circumference and at least one force-enhancing device extending laterally from the outer circumference of the base, wherein the base is configured for arrangement on the container such that the container is configured for connection to the base in a fluid-tight manner, and
  - a closure part comprising:
    - a closure cap having an outer circumferential perimeter smaller than the outer circumference of the base, the outer circumferential perimeter of the closure cap connected to the base via a predetermined breaking point, and at least one force-enhancing device extending laterally from the outer circumference of the closure cap, wherein:
- the at least one force-enhancing device of the base and the at least one force-enhancinq device of the closure part are configured to be operated by a single hand to move the base and the closure part relative to each other in a force-assisted manner to destroy the predetermined breaking point, wherein the force-enhancing devices enclose there between an angle (α), viewed in the circumferential direction of the closure, which corresponds at least substantially to the required amount of rotation of the closure part with respect to the base for destroying the predetermined breaking point.

2. The container apparatus according to claim 1, wherein the movement of the base and the closure part relative to each other is a rotary movement of the closure part with respect to the base in an opening direction of the closure part.

3. The container apparatus according to claim 1, wherein each of the force-enhancing devices is a handle substantially projecting radially from both the base and the closure part with respect to the axis of rotation of the rotary movement.

4. The container apparatus according to claim 3, wherein each of the handles is a lever.

5. The container apparatus according to claim 1, wherein the angle is within a range of about 20° to 50°.

6. The container apparatus according to claim 5, wherein the range is about 30° to 40°.

7. The container apparatus according to claim 3, wherein a force application point on the handle of the base and a force application point on the handle of the closure part are substantially located on a joint circumference (U) around the axis of rotation of the rotary movement.

8. The container apparatus according to claim 3, wherein the handle of the base is configured to be sector-shaped in a top view such that it projects from the handle of the closure part while enclosing the angle within a range of about 20° to 50° on both sides in the circumferential direction.

9. The container apparatus according to claim 8, where the range is about 30° to 40°.

10. The container apparatus according to claim 3, wherein each of the handles is diametrically opposed to each other.

11. The container apparatus according to claim 1, wherein the container is configured to hold medical fluids.

12. A container apparatus comprising:
- a container having an opening; and
- a tamperproof closure arranged on the opening of the container, the tamperproof closure including:
  - a base configured for arrangement on the opening of the container wherein the container is configured for connection to the base in a fluid-tight manner, and
  - a closure part connected to the base via a predetermined breaking point, wherein:
- each of the base and the closure part has at least one single-handedly operable force-enhancing device by which a movement of the base and the closure part relative to each other can be force-assisted in terms of destruction of the predetermined breaking point, wherein the force-enhancing devices enclose there between an angle (α), viewed in the circumferential direction of the closure, which corresponds at least substantially to the required amount of rotation of the closure part with respect to the base for destroying the predetermined breaking point, and
- the force-enhancing device of the base is configured as a first land and a second land projecting radially outward from the base.

13. The container apparatus according to claim 12, wherein the first land and the second land each have free ends distal to the base, the two free ends interconnected by a bridge.

14. The container apparatus according to claim 12, wherein the force-enhancing device of the closure part is a handle.

15. The container apparatus according to claim 12, wherein the force-enhancing device of the closure part is a lever.

16. The container apparatus according to claim 12, wherein the movement of the base and the closure part relative to each other is effectuated between the first land of the base and the force-enhancing device of the closure part.

17. The container apparatus according to claim 12, wherein the movement of the base and the closure part relative to each other is effectuated between the second land of the base and the force-enhancing device of the closure part.

18. A container apparatus comprising:
- a container having an opening; and
- a tamperproof closure arranged on the opening of the container, the tamperproof closure including:
  - a base configured for arrangement on the opening of the container wherein the container is configured for connection to the base in a fluid-tight manner, and
  - a closure part connected to the base via a predetermined breaking point, wherein:
- each of the base and the closure part has at least one single-handedly operable force-enhancing device by which a movement of the base and the closure part relative to each other can be force-assisted in terms of destruction of the predetermined breaking point, wherein the force-enhancing devices enclose there between an angle (α), viewed in the circumferential direction of the closure, which corresponds at least substantially to the required amount of rotation of the closure part with respect to the base for destroying the predetermined breaking point, each of the force-enhancing devices is a handle substantially projecting radially from both the base and the closure part with respect to the axis of rotation of the rotary movement, the handle of the base is configured to be sector-shaped in a top view such that it projects from the handle of the closure part while enclosing the angle within a range of about 20° to 50° on both sides in the circumferential direction, and the solid sector is provided with at least one slit-shaped breakthrough.

19. A container apparatus comprising:

a container having an opening; and a tamperproof closure arranged on the opening of the container, the tamperproof closure including:

a base configured for arrangement on the opening of the container wherein the container is configured for connection to the base in a fluid-tight manner, and a closure part connected to the base via a predetermined breaking point, wherein:

each of the base and the closure part has at least one single-handedly operable force-enhancing device by which a movement of the base and the closure part relative to each other can be force-assisted in terms of destruction of the predetermined breaking point, wherein the force-enhancing devices enclose there between an angle ($\alpha$), viewed in the circumferential direction of the closure, which corresponds at least substantially to the required amount of rotation of the closure part with respect to the base for destroying the predetermined breaking point, each of the force-enhancing devices is a handle substantially projecting radially from both the base and the closure part with respect to the axis of rotation of the rotary movement, the handle of the base is configured to be sector-shaped in a top view such that it projects from the handle of the closure part while enclosing the angle within a range of about 20° to 50° on both sides in the circumferential direction, and the solid sector has a surface facing the force-enhancing device of the closure part, the surface including a ramp continuously raised in a direction of the rotation of the closure part with respect to the base.

* * * * *